United States Patent
Gittard (10) Patent No.: US 9,414,946 B2
(45) Date of Patent: Aug. 16, 2016

(54) TISSUE INGROWTH INTESTINAL BYPASS SLEEVE AND METHOD OF DEPLOYMENT

(71) Applicant: Shaun D. Gittard, Winston Salem, NC (US)

(72) Inventor: Shaun D. Gittard, Winston Salem, NC (US)

(73) Assignee: Cook Medical Technologies LLC, Bloomington, IN (US)

(*) Notice: Subject to any disclaimer, the term of this patent is extended or adjusted under 35 U.S.C. 154(b) by 175 days.

(21) Appl. No.: 14/200,419

(22) Filed: Mar. 7, 2014

(65) Prior Publication Data

US 2014/0257164 A1  Sep. 11, 2014

Related U.S. Application Data

(60) Provisional application No. 61/774,123, filed on Mar. 7, 2013.

(51) Int. Cl.
*A61M 19/00* (2006.01)
*A61F 5/00* (2006.01)
*A61M 25/04* (2006.01)

(52) U.S. Cl.
CPC ............ *A61F 5/0076* (2013.01); *A61F 5/0089* (2013.01); *A61M 25/04* (2013.01)

(58) Field of Classification Search
CPC .... A61F 5/0076; A61F 5/0089; A61M 25/04; A61M 25/10

USPC ......................................... 604/8, 9; 623/1.12
See application file for complete search history.

(56) References Cited

U.S. PATENT DOCUMENTS

| | | | | |
|---|---|---|---|---|
| 5,741,326 | A | * | 4/1998 | Solovay .................... A61F 2/07 623/2.25 |
| 5,743,874 | A | * | 4/1998 | Fischell .................... A61F 2/95 604/103.04 |
| 7,220,284 | B2 | | 5/2007 | Kagan et al. |
| 7,708,752 | B2 | | 5/2010 | Durgin |
| 8,012,135 | B2 | | 9/2011 | Dann et al. |
| 8,100,931 | B2 | | 1/2012 | Baker et al. |
| 8,137,301 | B2 | * | 3/2012 | Levine ............... A61B 17/0401 604/8 |
| 8,182,441 | B2 | | 5/2012 | Swain et al. |
| 8,182,459 | B2 | | 5/2012 | Dann et al. |
| 2006/0282152 | A1 | * | 12/2006 | Beyerlein ................ A61F 2/966 623/1.11 |
| 2007/0150063 | A1 | * | 6/2007 | Ruberte .................. A61F 2/442 623/17.16 |
| 2008/0215076 | A1 | | 9/2008 | Baker |

* cited by examiner

*Primary Examiner* — Leslie Deak
(74) *Attorney, Agent, or Firm* — Brinks Gilson & Lione; John C. Bacoch (57) ABSTRACT

A device and method for deploying an intestinal sleeve is disclosed. The intestinal sleeve has an impermeable layer and a tissue ingrowth layer. The intestinal sleeve is temporarily anchored to the wall of a patient's duodenum and the wall tissue grows into the tissue ingrowth layer anchoring the intestinal sleeve within the patient's duodenum.

17 Claims, 6 Drawing Sheets

TISSUE INGROWTH INTESTINAL BYPASS SLEEVE AND METHOD OF DEPLOYMENT

FIELD

Embodiments of the present invention relate to the field of implants for treating obesity and Type II diabetes. More specifically embodiments of the present invention relate to systems and methods for deploying implants for reducing the ability of the body to absorb nutrients.

BACKGROUND

The human body absorbs nutrients through the digestive system. Food is introduced through the mouth where a person's teeth masticate the food into smaller pieces. Saliva in the mouth begins the digestion of starch in the food. A person then swallows the food, transporting the food through the esophagus into the stomach. In the stomach, the food is mixed with gastric juice which begins the digestion of protein in the food. The stomach mixes the food with other enzymes. After a period of time, the pyloric sphincter opens at the bottom of the stomach allowing the food to pass into the duodenum where the food mixes with more enzymes. The food continues into the small intestine, where digestion continues and nutrients are adsorbed into the bloodstream. The large majority of the absorption of nutrients occurs in the small intestine. The remaining material is transported to the large intestine where water is absorbed before waste is eliminated from the body.

Reducing the ability of the body to absorb nutrients has been shown to be an effective means of weight loss and treatment of Type II diabetes. Past treatments for reducing the ability of the body to adsorb nutrients included gastric bypasses, in which a portion of the digestive system is bypassed, gastrectomy in which the functional volume of the stomach is reduced, and intestinal and/or stomach sleeves, in which the sleeves inhibit the absorption of nutrients. Current intestinal sleeves are placed proximate the pyloric sphincter, with part of the intestinal sleeve in the distal end of the stomach and part of the intestinal sleeve in the duodenum. Current devices may cause sores in the stomach and intestine from the intestinal sleeve rubbing and cutting into tissue as well as twisting and subsequent stricture of the sleeve.

It is difficult to anchor a device in the duodenum of a patient because the mucosal layer of the duodenum continually renews itself by sloughing off. Thus any attachment to the mucosal layer eventually fails as the mucosal layer sloughs. It would be beneficial to develop an intestinal sleeve that does not rub and cut into tissue, but is able to remain in place despite any sloughing of tissue adjacent the intestinal sleeve.

SUMMARY

Embodiments of the invention include a catheter assembly for deploying an endoluminal sleeve. The catheter assembly includes a first catheter, a conical cap, a balloon, a sleeve, and a second catheter. The first catheter has a distal portion, a proximal portion, and a first outside diameter. The conical cap is located at a distal end of the first catheter and has a base diameter greater than the first outside diameter. The balloon is disposed at the distal portion of the first catheter and has an inflated configuration in which a balloon diameter is greater than the base diameter and a deflated configuration in which the balloon diameter is less than the base diameter. The sleeve has a lumen and the balloon is internal to the lumen. The sleeve is wrapped about an axis of the catheter assembly and has a porous outer ingrowth layer and an impermeable inner layer. The outer ingrowth layer has an outer surface with at least one temporary attachment mechanism for attachment to a body lumen. The second catheter is disposed about the first catheter and is slidable from a first position in which the second catheter covers the balloon and engages the conical cap and a second position in which the second catheter does not cover the balloon.

Another embodiment includes a method for deploying an intestinal bypass sleeve. In the method a distal end of a catheter assembly is guided to the duodenum of a patient. The distal end of the catheter assembly has a balloon, an intestinal bypass sleeve having an impermeable inner layer and an ingrowth outer layer disposed about the balloon, and an introducer sheath covering the intestinal bypass sleeve. The introducer sheath of the catheter assembly is retracted to uncover at least a portion of the intestinal bypass sleeve. The balloon is inflated to expand at least a portion the intestinal bypass sleeve within the duodenum of the patient. The ingrowth outer layer is anchored to the wall of the duodenum of the patient through a temporary anchor mechanism, wherein the ingrowth outer layer is anchored only to the duodenum along the entire length of the intestinal bypass sleeve. The balloon is deflated leaving the intestinal bypass sleeve anchored to the wall of the duodenum and the distal end of the catheter assembly is removed from the duodenum of the patient. Tissue ingrowth is then promoted into the ingrowth outer layer to durably anchor the intestinal bypass sleeve within the duodenum.

BRIEF DESCRIPTION OF THE DRAWINGS

To further clarify the above and other advantages and features of the one or more present inventions, reference to specific embodiments thereof are illustrated in the appended drawings. The drawings depict only typical embodiments and are therefore not to be considered limiting. One or more embodiments will be described and explained with additional specificity and detail through the use of the accompanying drawings in which.

The drawings are not necessarily to scale.

DETAILED DESCRIPTION

As used herein, "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C" and "A, B, and/or C" means A alone, B alone, C alone, A and B together, A and C together, B and C together, or A, B and C together.

Various embodiments of the present inventions are set forth in the attached figures and in the Detailed Description as provided herein and as embodied by the claims. The embodiments will be described in relation to an intestinal sleeve, but one of ordinary skill in the art would recognize that the system and methods are applicable more generally to an endoluminal sleeve and the deployment of the endoluminal sleeve in a body lumen. It should be understood, however, that this Detailed Description does not contain all of the aspects and embodiments of the one or more present inventions, is not meant to be limiting or restrictive in any manner, and that the invention(s) as disclosed herein is/are and will be understood by those of ordinary skill in the art to encompass obvious improvements and modifications thereto.

In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous. Additional advantages of the present invention will become readily apparent from the following discussion, particularly when taken together with the accompanying drawings.

Figure 1:
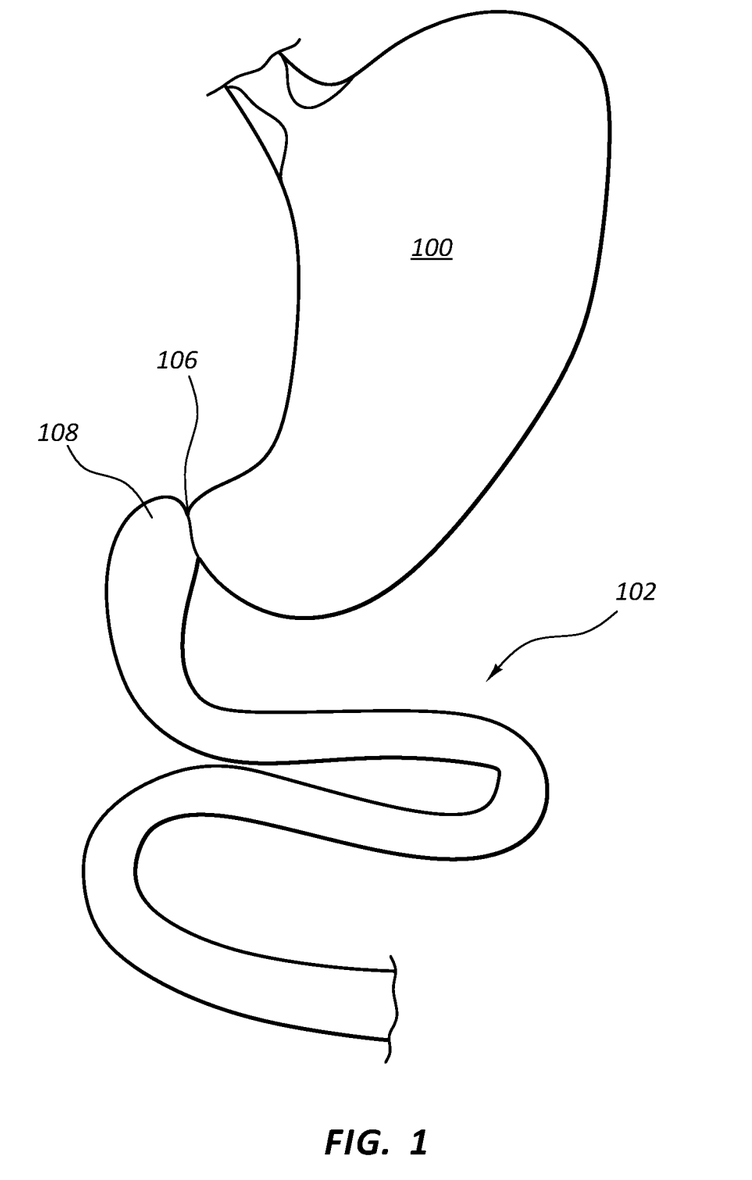
FIG. 1 is a schematic of a stomach and upper lower intestine including the duodenum.

FIG. 1 is a cross-sectional schematic of a stomach 100 and a portion of a small intestine 102. A ring like muscle, the pyloric sphincter 106, separates the interior of the stomach 100 and the interior of the small intestine 102. In a contracted state, the pyloric sphincter 106 inhibits material from passing between the stomach 100 and the small intestine 102. When the pyloric sphincter 106 relaxes, the content of the stomach 100 may be passed into the small intestine 102. Just beyond the pyloric sphincter 106 is the first section of the small intestine 102, termed the duodenum 108.

Figure 2:
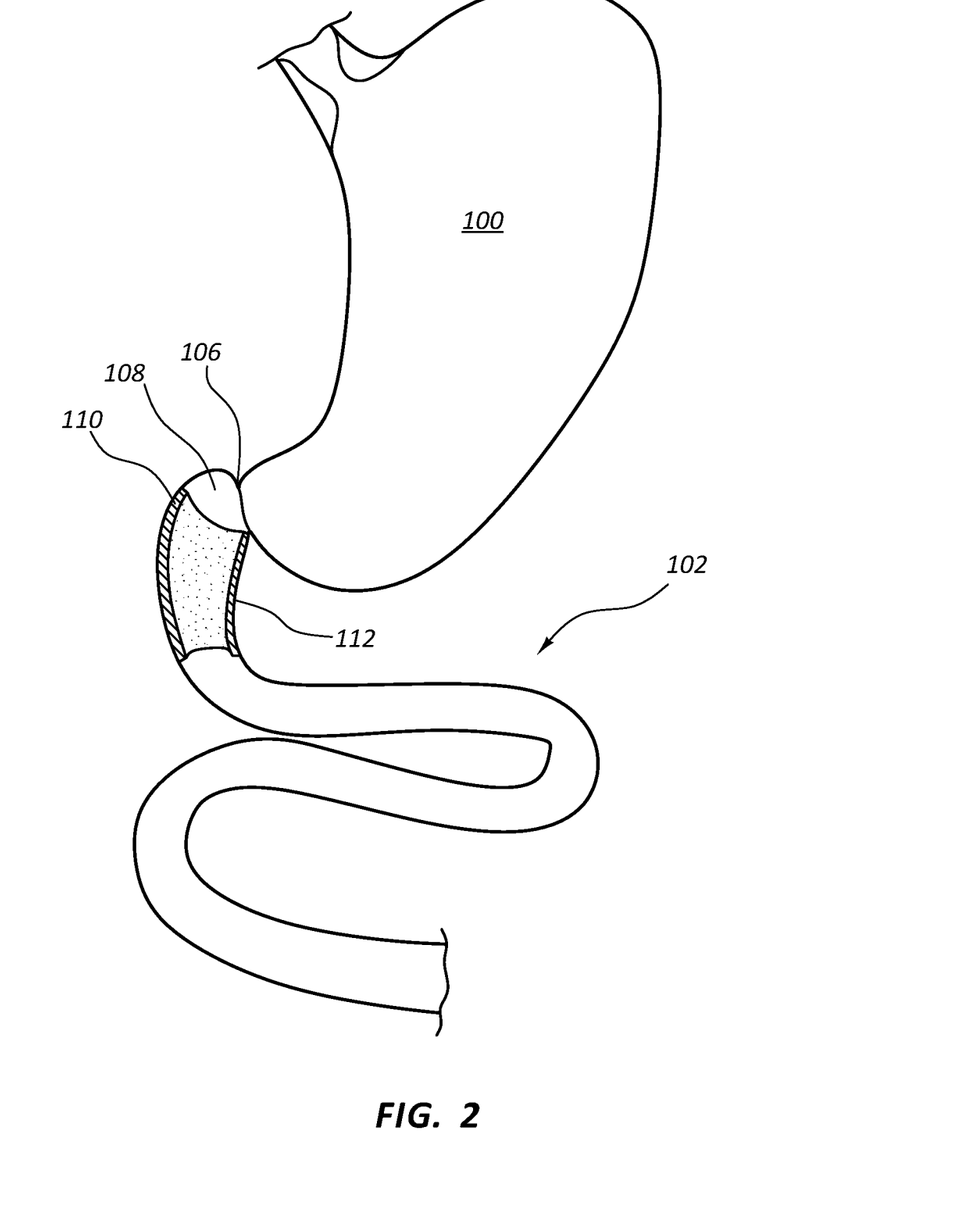
FIG. 2 is a schematic of a stomach and upper lower intestine including the duodenum illustrating an intestinal sleeve deployed in the duodenum.

FIG. 2 is a cross-sectional schematic of the stomach 100 of FIG. 1, showing an embodiment of a tissue ingrowth intestinal sleeve 110 fixed in place. The tissue ingrowth intestinal sleeve 110 is comprised of a multi-layer cylindrical membrane fixed to a wall 112 of the duodenum 108. The multi-layer cylindrical membrane is comprised of an inner layer of impermeable material and an outer layer facing the wall 112 that promotes tissue ingrowth. Nutrients passing from the stomach 100 into the duodenum 108 are inhibited from absorption by the tissue ingrowth intestinal sleeve 110.

Figure 3:
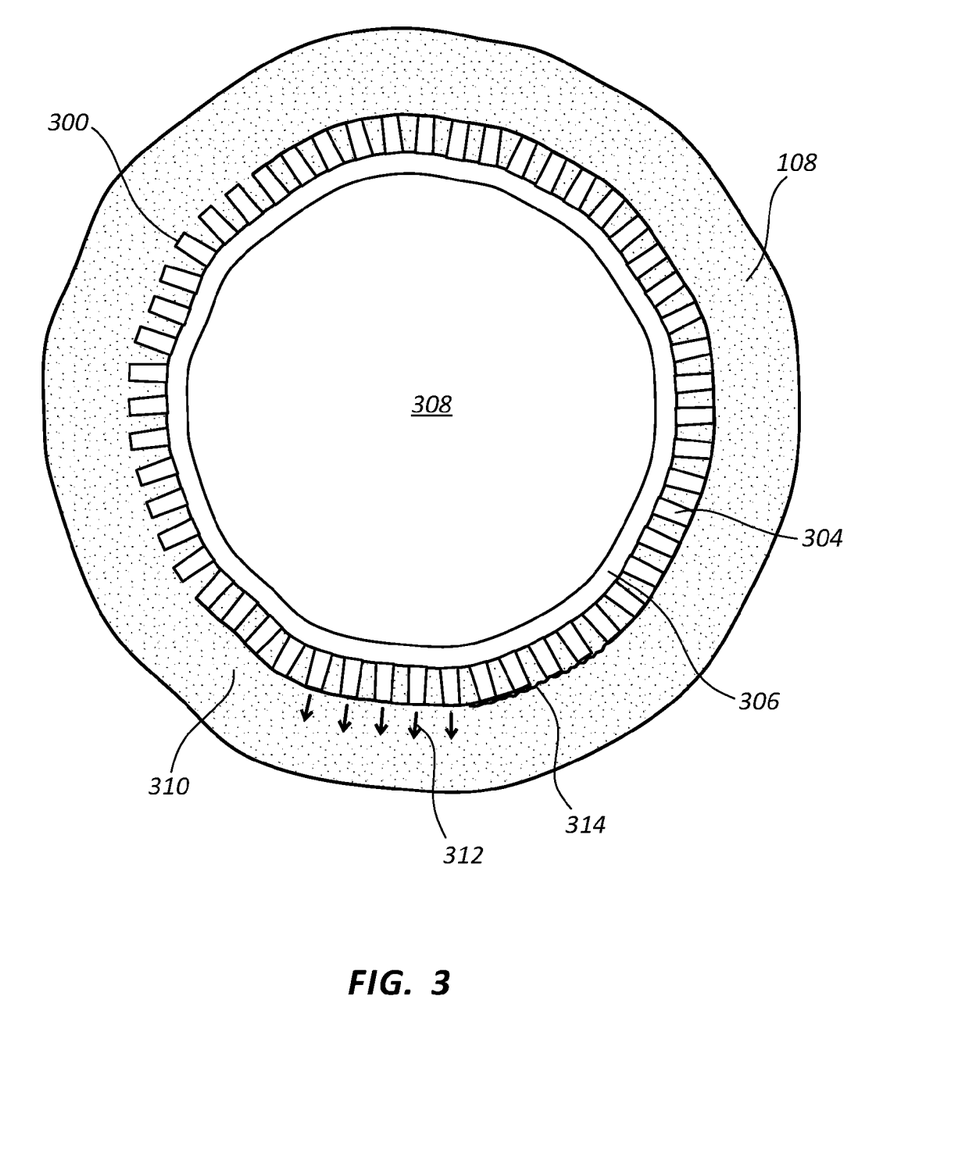
FIG. 3 is a schematic of an intestinal sleeve disposed in the duodenum with a temporary anchor.

FIG. 3 is a cross-section of an exemplary intestinal sleeve 300 disposed in the duodenum 108. The intestinal sleeve 300 is comprised of an outer layer 304 and an inner layer 306 bonded together. In some embodiments a third inner layer (not shown) may be present between the inner layer 306 and the outer layer 304 to promote bonding between the two layers. The inner layer 306 is comprised of a material that inhibits nutrients from passing through to the duodenum 308. The material may be impermeable to nutrients. Exemplary materials for the inner layer 306 include fluoropolymers (PTFE, FEP, etc), polyethylene, polypropylene, polyurethane, PEEK, PET, nylons, etc. The outer layer 304 is comprised of a material that promotes tissue ingrowth from the duodenum 108. Examples of suitable materials include porous materials such as meshes, woven fabric, non-woven fabric, pocketed materials, materials with pores, and extracellular matrix (ECM) and other collagen-based materials including ECM or collagen-based foams. Extracellular matrix (ECM) materials, including those derived from submucosa and other tissues, are known tissue graft materials used in tissue graft applications. See, e.g., U.S. Pat. Nos. 4,902,508, 4,956,178, 5,281,422, 5,372,821, 5,554,389, 6,099,567, and 6,206,931. These materials typically are derived from a variety of biological sources including, for example, small intestine, stomach, urinary bladder, skin, pericardium, dura mater, fascia, and the like. These materials may be decelluarized and processed to retain natural growth factors and other bioactive constituents, or they may be cross-linked with an agent such as glutaraldehyde. Further information on processing an ECM material for medical use can be found in U.S. Pat. No. 8,329,219. All of the above referenced patents and their teachings are expressly incorporated by reference herein.

In some embodiments the intestinal sleeve 300 may include a plurality of anchors for attaching the intestinal sleeve 300 to the duodenum 108. Because tissue ingrowth is unable to immediately fasten the intestinal sleeve 300, the plurality of anchors secure the intestinal sleeve 300 until sufficient ingrowth occurs to durably anchor the intestinal sleeve 300. The plurality of anchors for fastening the intestinal sleeve 300 may include spikes 310, barbs 312, spurs, combinations of the foregoing, or other suitable fastening techniques as known in the art. In some embodiments an adhesive 314 may comprise the plurality of anchors. The plurality of anchors may be biodegradable/bioabsorbable such that the plurality of anchors dissolve as tissue ingrowth occurs. The plurality of anchors secures the intestinal sleeve 300 substantially along the entire length of the intestinal sleeve 300, such that the intestinal sleeve 300 does not migrate during peristalsis of the duodenum 108. This reduces irritation and promotes tissue ingrowth.

Figure 4:
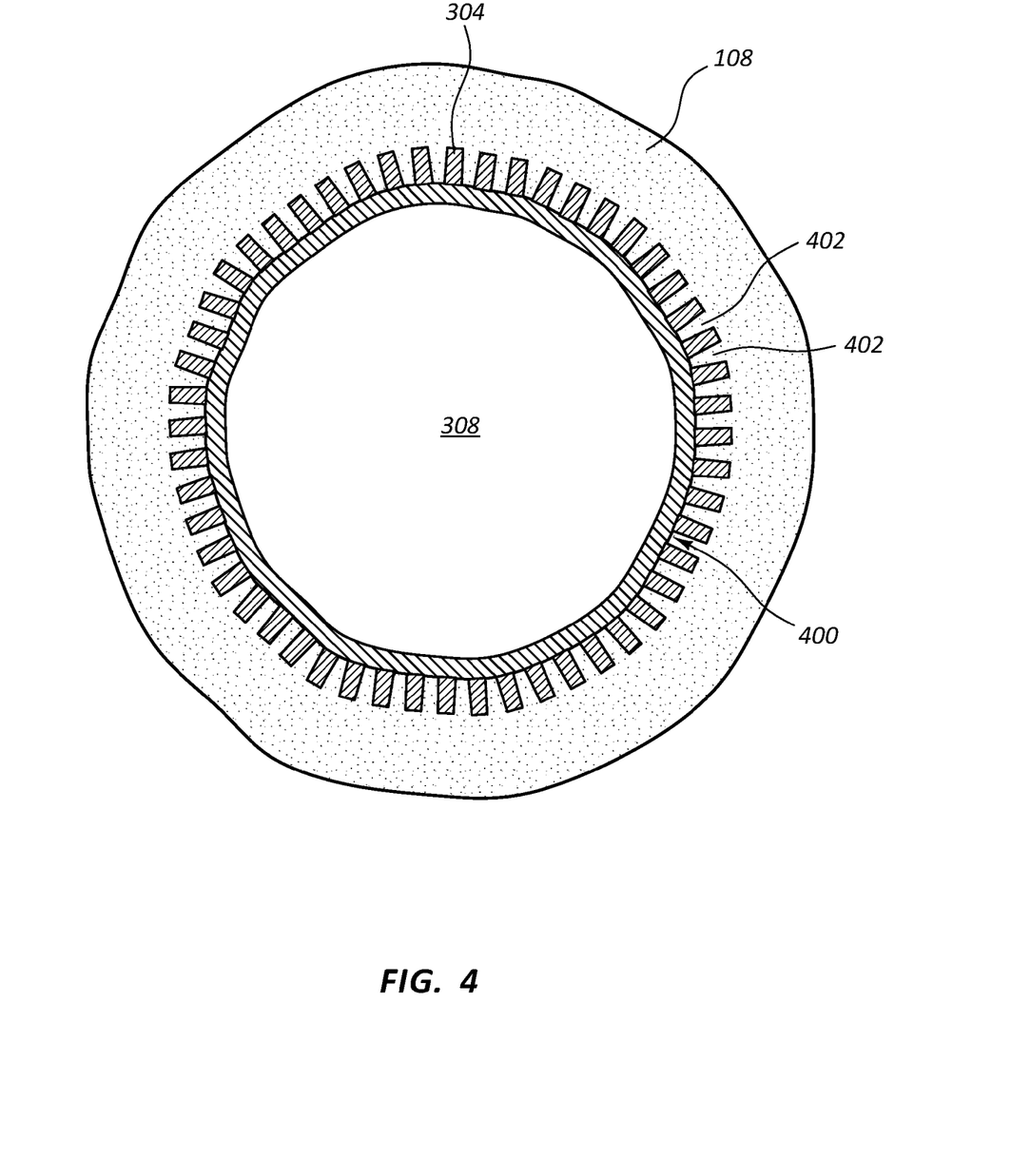
FIG. 4 is a schematic of an intestinal sleeve disposed in the duodenum with tissue having grown into the outer layer of the intestinal sleeve to form a durable anchor.

FIG. 4 illustrates a cross-section of the intestinal sleeve 300 of FIG. 3, after tissue ingrowth has occurred. The tissue of the duodenum 108 surrounding the intestinal sleeve 300 has grown into the pores 402 of the outer layer 304 of the intestinal sleeve 300. The tissue ingrowth 400 is sufficient to hold the intestinal sleeve 300 in place, and the plurality of anchors for fastening are no longer necessary. In embodiments in which a biodegradable/bioabsorable material is used, the spikes 310, barbs 312, and adhesive 314 are no longer present on the outer layer 304.

Figure 5:
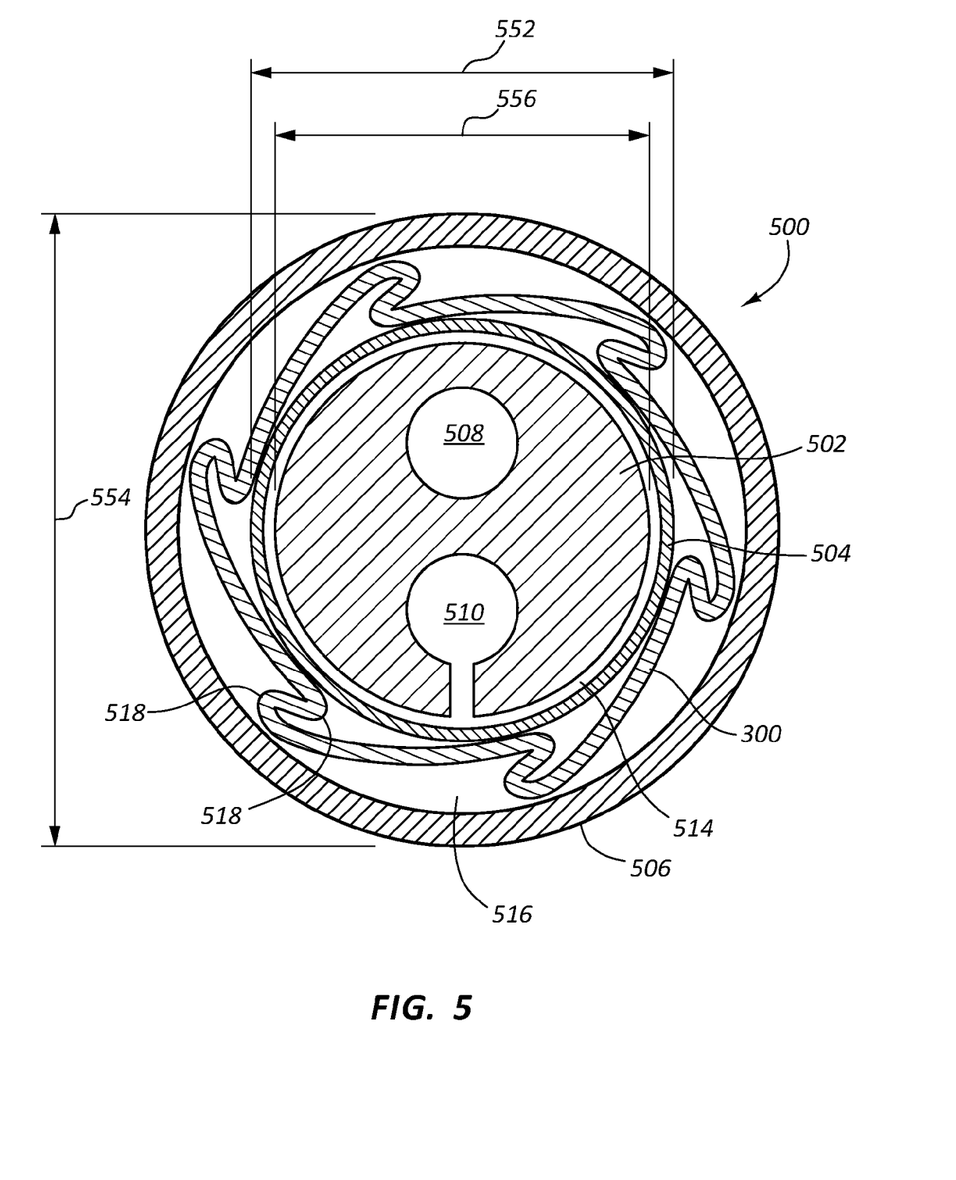
FIG. 5 is a cross sectional view of a catheter assembly for deploying the intestinal sleeve.
Figure 7:
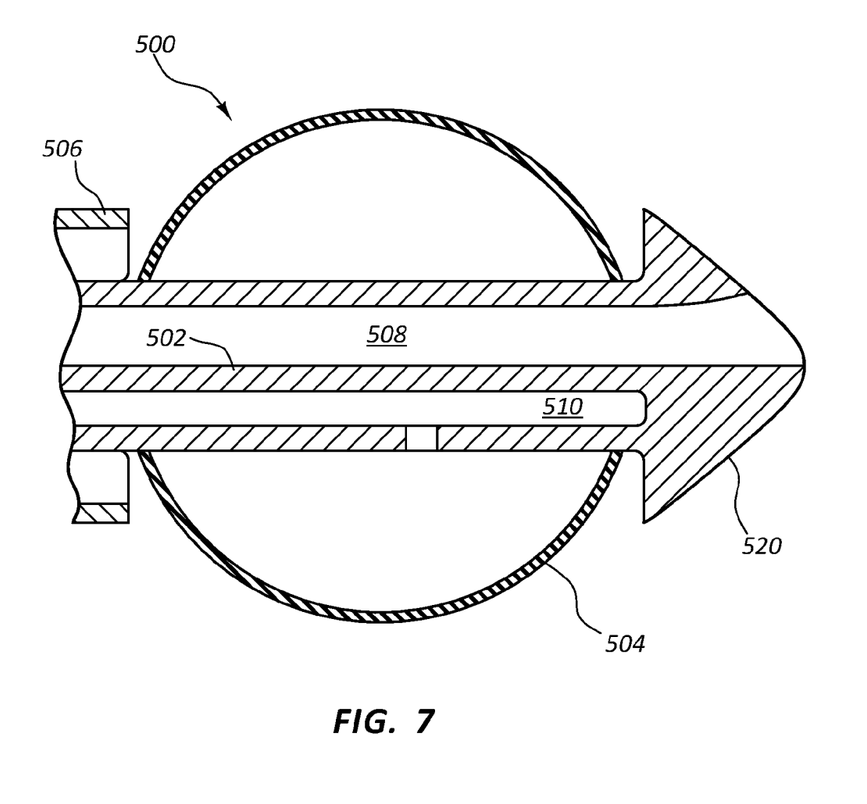
FIG. 7 is a lateral cross sectional view of the catheter assembly of FIG. 5 with the balloon expanded.

FIG. 5 illustrates a simplified cross sectional view of a catheter assembly 500 for delivering the intestinal sleeve 300 to the duodenum 108. The catheter assembly 500 is comprised of a first catheter 502, a balloon 504, and a second catheter 506. The first catheter 502 may be a balloon catheter and the second catheter 506 may be an introducer sleeve. FIG. 5 illustrates a simplified cross sectional view of the intestinal sleeve 300 being wrapped around the balloon 504. The first catheter 502 includes a first lumen 508 through which a wire guide may pass. The first catheter 502 may have a conical cap to reduce potential trauma as the catheter assembly 500 is guided to the duodenum 108. The conical cap has a base diameter that is greater than the diameter of the first catheter 502. The balloon 504 has an uninflated configuration shown in FIG. 5 in which the balloon 504 is collapsed and an inflated configuration shown in FIG. 7 in which the balloon 504 is expanded. In the uninflated configuration, the diameter of the balloon 504 is greater than a diameter of the first catheter 502, but less than the base diameter. In the inflated condition, the diameter of the balloon 504 extends beyond the base diameter, as shown in FIG. 7. In use the wire guide passes through the first 508 and is guided to a treatment site. The catheter assembly 500 may be slid over the guide wire to reach the treatment site. A second lumen 510 extends the length of the first catheter 502 and provides fluid communication from a proximal location to the distal end of the first 502 catheter. A port 512 provides fluid communication between an inner volume 514 of the balloon 504 and the second lumen 510. The balloon 504 is illustrated in this simplified view as a uniform circle, but in some embodiments may be folded having folds with a cylindrical central portion. This allows the use of a balloon 504 with limited elasticity. A space 516 exists between the balloon 504 and the second catheter 506 for housing the intestinal sleeve 300. The intestinal sleeve 300 may have folds 518 enabling the intestinal sleeve 300 within the space 516.

Figure 6:
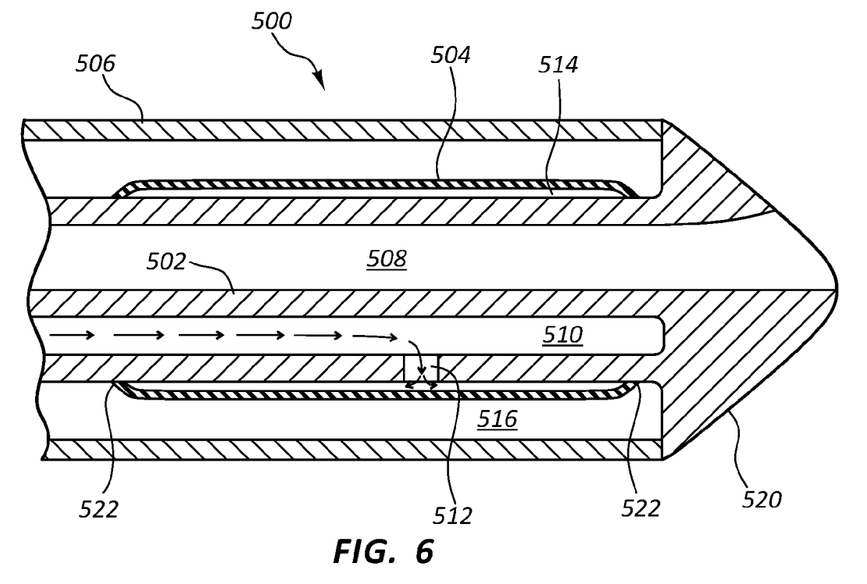
FIG. 6 is a lateral cross sectional view of the catheter assembly of FIG. 5.

FIG. 6 illustrates a sectional side view of the catheter assembly of FIG. 5. The intestinal sleeve 300 is not shown in this figure for clarity, but would be disposed in the space 516 shown between the balloon 504 and the second catheter 506. The first lumen 508 extends through a conical tip 520 of the first catheter 502 such that the first catheter 502 may be slid over a guidewire. The second lumen 510 is closed at the end so that fluid is only able to escape the lumen by passing through port 512 into the balloon 504. The balloon 504 is secured to the first catheter 502 at a proximal end 522 and a distal end 524. When fluid is delivered to the interior of the balloon 504 through the port 512, the balloon 504 expands outwardly.

FIG. 7 illustrates the section side view of FIG. 6, with the exception that the second catheter 506 has been retracted and the balloon 504 inflated. A method of deploying the intestinal sleeve 300 will now be described in relation to FIGS. 1, 6, and 7. Initially the distal end of the catheter assembly 500 is guided to the duodenum 108 of a patient. A wire guide may be in place extending from a location external to the patient to the duodenum 108. The catheter assembly 500 may then be inserted over the wire guide such that the wire guide passes through the first lumen 508. The catheter assembly 500 may be delivered through the patient's esophagus.

Once the distal end of the catheter assembly 500 is in place in the duodenum 108, the second catheter 506 is retracted relative to the first catheter 502. This exposes the space 516 housing the intestinal sleeve 300. The first catheter 502 may remain fixed and the second catheter 506 is moved proximally to retract the second catheter 506. In other embodiments the second catheter 506 may remain fixed and the first catheter 502 extended, which results in the second catheter 506 being retracted thereby exposing at least a portion of the space 516.

With the second catheter 506 retracted, the intestinal sleeve 300 is exposed to the duodenum 108. The intestinal sleeve 300 can then be expanded by inflating the balloon 504 through the through the second lumen 510 and the port 512. In other embodiments the balloon 504 may be expanded through other means, such as axially compressing the balloon 504. The balloon 504 is expanded until at least a portion of the intestinal sleeve 300 contacts a wall 112 of the duodenum 108.

The intestinal sleeve 300 is anchored to the wall 112 using a temporary attachment mechanism to hold the intestinal sleeve 300 in place until tissue ingrowth can occur. The intestinal sleeve 300 may be anchored to the wall 112 through the use of an adhesive, suction, pressure, or a mechanical fixture such as a spike, barb, tack, or spur. In some embodiment the temporary attachment mechanism may be biodegradable/bioabsorbable such that it will eventually dissolve. The inflation of the balloon 504 may cause the intestinal sleeve 300 to anchor to the wall 112. For example, the balloon 504 could be inflated to a pressure sufficient to cause a barb to puncture the wall 112, or the balloon 504 may hold the intestinal sleeve 300 against the wall 112 until the adhesive adheres to the wall 112.

After the intestinal sleeve 300 in temporarily anchored to the wall 112, the balloon 504 is deflated, leaving the intestinal sleeve 300 in place. In some embodiments the intestinal sleeve 300 may be longer than the balloon 504 such that only a portion of the intestinal sleeve 300 is attached to the wall 112. In such embodiments the balloon 504 can be repositioned with the intestinal sleeve 300 partially attached to the wall 112. Then, once repositioned, the balloon 504 is inflated again and another portion of the intestinal sleeve 300 is secured. This process may be repeated until the intestinal sleeve 300 is completely anchored to the wall 112 of the duodenum 108. The intestinal sleeve 300 is anchored only to the wall 112 of the duodenum 108 and does not extend through the pyloric sphincter.

The distal end of the catheter assembly 500 is then removed with the balloon 504 deflated. The intestinal sleeve 300 remains in place through the use of the temporary anchors. Tissue ingrowth is then promoted such that the tissue from the wall 112 of the duodenum 108 grows into the outer layer 304 of the intestinal sleeve 300. The tissue ingrowth in promoted through the use of the ingrowth promoting material in the outer layer 304 and by minimizing movement of the intestinal sleeve 300. As the tissue grows into the wall 112 of the intestinal sleeve 300, a durable anchor is formed. In embodiments in which the temporary anchors are biodegradable/bioabsorbable, the temporary anchors slowly dissolve as the tissue grows into the intestinal sleeve 300.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

What is claimed:

1. A catheter assembly for deploying an endoluminal sleeve, the catheter assembly having an axis and comprising:
    a first catheter having a distal portion, a proximal portion, and a first outside diameter;
    a balloon disposed at the distal portion of the first catheter, the balloon having an inflated configuration in which a balloon diameter is greater than the first outside diameter and a deflated configuration;
    a sleeve having a lumen, the balloon being internal to the lumen, the sleeve being wrapped about the catheter assembly axis and having a porous outer ingrowth layer and an impermeable inner layer, the outer ingrowth layer being configured to promote issue ingrowth and having an outer surface with at least one temporary attachment mechanism for attachment to a body lumen; and
    a second catheter disposed about the first catheter and being slidable from a first position in which the second catheter covers the balloon and a second position in which the second catheter does not cover the balloon.

2. The catheter assembly of claim 1 further comprising a conical cap located at a distal end of the balloon catheter, the conical cap having a base diameter greater than the first outside diameter, wherein the balloon in the deflated configuration has an outside diameter less than the base diameter and wherein the second catheter engages the conical cap in the first position.

3. The catheter assembly of claim 2 wherein the plurality of anchors is selected from the group consisting of spikes, barbs, tacks, and spurs.

4. The catheter assembly of claim 2 wherein the plurality of anchors are biodegradable.

5. The catheter assembly of claim 2 wherein the plurality of anchors are bio absorbable.

6. The catheter assembly of claim 1 wherein the at least one temporary attachment mechanism comprises a plurality of anchors.

7. The catheter assembly of claim 1 wherein the at least one temporary attachment mechanism comprises an adhesive.

8. The catheter assembly of claim 1 wherein the outer ingrowth layer comprises a woven fabric.

9. The catheter assembly of claim 1 wherein the outer ingrowth layer comprises a mesh.

10. The catheter assembly of claim 1 wherein the outer ingrowth layer comprises a plurality of pores.

11. The catheter assembly of claim 1 wherein the outer ingrowth layer is comprised of small intestine submucosa.

12. The method of claim 11 further comprising allowing the temporary anchor mechanism to dissolve within the patient.

13. The method of claim 11 wherein the temporary anchor mechanism is selected from the group consisting of adhesive, spikes, barbs, tacks, and spurs.

14. The method of claim 11 wherein promoting tissue ingrowth comprises leaving the intestinal bypass sleeve within the duodenum for an extended length of time.

15. The method of claim 11 wherein the catheter assembly is guided to the duodenum through the patient's esophagus.

16. The method of claim 11 wherein the introducer catheter is retracted while maintaining the position of the intestinal bypass sleeve.

17. A method for deploying an intestinal bypass sleeve comprising:
    guiding a distal end of a catheter assembly to the duodenum of a patient, the distal end of the catheter assembly having a balloon, an intestinal bypass sleeve having an impermeable inner layer and an ingrowth outer layer disposed about the balloon, and an introducer sheath covering the intestinal bypass sleeve;
    retracting the introducer sheath of the catheter assembly to uncover at least a portion of the intestinal bypass sleeve;
    inflating the balloon to expand at least a portion the intestinal bypass sleeve within the duodenum of the patient;
    anchoring the ingrowth outer layer to the wall of the duodenum of the patient through a temporary anchor mechanism, wherein the ingrowth outer layer is anchored only to the duodenum along the entire length of the intestinal bypass sleeve;
    deflating the balloon leaving the intestinal bypass sleeve anchored to the wall of the duodenum;
    removing the distal end of the catheter assembly from the duodenum of the patient; and
    promoting tissue ingrowth into the ingrowth outer layer to durably anchor the intestinal bypass sleeve within the duodenum.

* * * * *